United States Patent [19]

Mattox

[11] Patent Number: 5,430,046
[45] Date of Patent: Jul. 4, 1995

[54] SOLID 3-ISOTHIAZOLONE BIOCIDAL CONCENTRATES

[75] Inventor: John R. Mattox, Perkasie, Pa.

[73] Assignee: Rohm and Haas Company, Philadelphia, Pa.

[21] Appl. No.: 209,799

[22] Filed: Mar. 11, 1994

[51] Int. Cl.⁶ .................. A01N 43/80; C07D 275/03
[52] U.S. Cl. .................................. 514/372; 514/373; 548/209; 548/213
[58] Field of Search ................ 514/372, 373; 548/209, 548/213

[56] References Cited

U.S. PATENT DOCUMENTS

| | | | |
|---|---|---|---|
| 3,761,488 | 9/1973 | Lewis et al. | 260/302 |
| 4,105,431 | 8/1978 | Lewis et al. | 71/67 |
| 4,252,694 | 2/1981 | Lewis et al. | 252/545 |
| 4,265,899 | 5/1981 | Lewis et al. | 424/270 |
| 4,279,762 | 7/1981 | Lewis et al. | 252/47 |

Primary Examiner—Richard L. Raymond
Attorney, Agent, or Firm—Michael B. Fein

[57] ABSTRACT

Composition as a highly useful concentrated biocide, said composition being solid at 20° C., easily meltable and solidifyable, capable of undergoing remelt and resolidification without loss of homogeneity and method.

10 Claims, No Drawings

SOLID 3-ISOTHIAZOLONE BIOCIDAL CONCENTRATES

BACKGROUND OF THE INVENTION

1. Field of the Invention

This invention relates to solid biocidal concentrates.

2. Prior Art

Isothiazolones are described in U.S. Pat. Nos. 3,761,488; 4,105,431; 4,252,694; 4,265,899 and 4,279,762, and elsewhere. Their use as microbicides is well known.

It is the principal object of this invention to provide solid biocidal concentrate compositions which overcome disadvantages of the prior art.

SUMMARY OF THE INVENTION

It is an object of the present invention to provide a solid, biocidal concentrate which remains homogeneous after repeated solid/melt cycles. These solid concentrates are useful for preserving industrial coatings, such as paints, elastomeric coatings, mastics, adhesives, sealants, and caulks; latexes, emulsions, and the like.

This object, and others which will become apparent from the following disclosure, are achieved by the present invention which comprises in one aspect a composition useful as a highly concentrated biocide, said composition being solid at 20° C., easily meltable and solidifyable, capable of undergoing remelt and resolidification without loss of homogeneity, and comprising:

A. a first component consisting of about 99 to 50 parts of a 3-isothiazolone of the formula

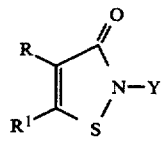

wherein R and $R^1$ are independently selected from hydrogen, halogen or R is a ($C_1$–$C_4$)alkyl group and $R^1$ is a hologen or R and $R^1$ may be joined to form an unsaturated 5- or 6-membered carbocyclic ring; Y is hydrogen, a substituted or unsubstituted ($C_1$–$C_{18}$)alkyl group, an unsubstituted or halo-substituted alkenyl or alkynyl of 2 to 8 carbon atoms, a cycloalkyl or substituted cycloalkyl of 3 to 12 carbon atoms, an aralkyl or halo-, ($C_1$–$C_4$)alkyl-, or ($C_1$–$C_4$)alkoxy-substituted aralkyl of up to 10 carbon atoms, or an aryl or halo-, ($C_1$–$C_4$)alkyl-, or ($C_1$–$C_4$)alkoxy-substituted aryl group of up to 10 carbon atoms; and B. a second component consisting of about 1 to 50 parts of a melting point depressant having a specific gravity of about 1.14 to about 1.24, being miscible in a melt of A., and chemically compatible with A.

In another aspect the invention comprises a method for inhibiting the growth of bacteria, fungi, yeast, or algae in a locus, which comprises incorporating onto or into the locus, in an amount which is effective to inhibit the growth of bacteria, fungi, yeast, or algae, the aforementioned composition.

DETAILED DESCRIPTION AND THE PREFERRED EMBODIMENTS

The term "microbicidal" (or "antimicrobial" or "biocidal") as used herein is intended to encompass, but is not restricted to, all bactericidal, fungicidal and algicidal activity.

By a substituted alkyl group is meant an alkyl group having one or more of its hydrogen atoms replaced by another substituent group. Examples of the substituted alkyl, alkenyl, or alkynyl groups which characterize the 3-isothiazolones of this invention include hydroxyalkyl, haloalkyl, cyanoalkyl, alkylaminoalkyl, and the like.

Representative Y substituents include methyl, ethyl, propyl, isopropyl, hexyl, octyl, cyclohexyl, phenethyl, benzyl, hydrogen, and the like. Y is preferably hydrogen, methyl, ethyl, octyl, phenethyl, and cyclohexyl.

The 3-isothiazolones to which Sis invention is applicable are those which are solid at 20° C. Among such compounds are 4,5-dichloro-2-octyl-3-isothiazolone, 2-octyl-3-isothiazolone, 5-chloro-2-methyl-3-isothiazolone, and 2-methyl-3-isothiazolone.

In certain applications, it is desirable for the end user to have a solid form of a biocide, such as where a very high concentration of active ingredient is required. However, such solid forms may present problems in some applications, such as increased difficulty in transfering the bulk material versus a liquid, which is easily pourable or pumpable. It is known that melting the solid and transferring the material as a melt overcomes this problem, but introduces other problems. Some solid biocides have a high melting point which makes heating large volumes of the material, such as drums, impractical. Also, as not all of the biocide may be needed at the same time, a drum may undergo repeated solid/melt cycles as it is heated to remove a portion of the biocide each time. This repeated heating and resolidifying may anneal the solid material, thereby increasing the temperature required to melt it and also increasing the time required for it to uniformly melt.

Low-melting, solid biocides, such as 3-isothiazolones, and more specifically 4,5-dichloro-2-octyl-3-isothiazolone, present additional problems during storage. Drums of solid biocide may be stored in warehouses for a period of time before being shipped to the end user. During this storage, temperature fluctuations in the warehouse may occur, resulting in melting and resolidifying of the stored, low-melting, solid biocide. When this occurs, the biocide may be annealed before the end user receives the material, making it more difficult to use.

The addition of a melting point depressant to the solid biocide will reduce the temperature required for melting of the solid and the time required for total melt, thus overcoming some of the problems of the prior art. However, after repeated melting and resolidifying, the material remaining in the drum has a tendency to stratify or become non-homogeneous in concentration. When a portion of the non-homogeneous biocide is used, the end user adds too much or too little biocide. Too much biocide may cause problems in the end product and too little biocide will be ineffective in the control of microorganisms. This non-homogeneity of concentration will also increase the temperature and time required for complete melting of the solid; i.e., once the solid starts to melt, it will take more heat and time to fully melt than it did initially.

It has been found that compositions formed from 3-isothiazolones and a melting point depressant having a specific gravity of about 1.14 to about 1.24, or a mixture of melting point depressants having said specific gravity, the depressant or mixture being miscible in the melt of the isothiazolone(s) and being chemically compatible with the isothiazolone(s) unexpectedly afford a composition which overcomes the problems of the prior art.

The compositions of the invention are solids having a high concentration of biocide, melt at a low temperature, do not anneal, and remain homogeneous after repeated solid/melt cycles.

Preferred melting point depressant systems are mixtures of one or more hydrocarbons (having specific gravities below 1 ) and one or more compounds selected from the group consisting of methylene chloride and propylene carbonate (having higher specific gravities), the mixture having a specific gravity of about 1.14 to about 1.24. Examples of suitable hydrocarbons are methyl naphthalene(s), phenyl xylyl ethane, bis(methylethyl)-1,1'-biphenyl, and mixtures of mono-, di-, and tri-isopropylbiphenyl.

More than one melting point depressant may be used, and in some cases it is preferred to do so. Preferred combinations include, but are not limited to, methyl naphthalene/propylene carbonate (34/66) and methyl naphthalene/methylene chloride (50/50).

Preferred compositions of the invention comprise from about 50 to 99 parts of the isothiazolone. Even more preferred compositions comprise from about 80 to 99 parts of the isothiazolone.

The melting point depressant is present in an amount of about 1 to 50 parts of said composition. It is preferred that the compositions of the invention comprise sufficient amount of said melting point depressant to lower the melting point of the isothiazolone by 5° C. More preferred compositions comprise sufficient amount of said melting point depressant to lower the melting point of the isothiazolone by 10° C.

Important applications of the solid biocidal concentrate compositions of the present invention include but are not limited to: inhibiting the growth of hard and soft marine fouling organisms, such as algae, tunicates, hydroids, bivalves, bryozoans, polycheate worms, sponges, and barnacles, on submerged structures, such as underwater surfaces of ships, piers, docks, pilings, fishnets, heat exchangers, dams, and piping structures, such as intake screens; inhibiting the growth of algae, bacteria and fungi in industrial coatings, such as paints, elastomeric coatings, mastics, adhesives, sealants, and caulks; wood treatments, such as pressure or vacuum impregnation or anti-sapstain treatments; controlling slime-producing algae, bacteria and fungi in pulp and papermills and cooling towers; latex emulsions, and joint cements; preserving cutting fluids; as a spray or dip treatment for textiles and leather to prevent mold growth; protecting paint films, especially exterior paints, from attack by algae which occurs during weathering of the paint film; protecting processing equipment from slime deposits during manufacture of cane and beet sugar; preventing microorganism buildup and deposits in air washer or scrubber systems and in industrial fresh water supply systems; preserving fuel; controlling microorganism contamination and deposits in oil field drilling fluids and muds, and in secondary petroleum recovery processes; preventing bacterial and fungal growth in paper coatings and coating processes; controlling bacterial and fungal growth and deposits during the manufacture of various specialty boards, e.g., cardboard and particle board; controlling bacterial and fungal growth in clay and pigment slurries of various types; as a hard surface disinfectant to prevent growth of bacteria and fungi on walls, floors, etc.; as a preservative for cosmetic and toiletry raw materials, floor polishes, fabric softeners, household and industrial cleaners; in swimming pools to prevent algae growth; inhibiting the growth of harmful bacteria, yeasts, fungi on plants, trees, fruits, seeds, or soil; preserving agricultural formulations, electrodeposition systems, diagnostic and reagent products, medical devices; protecting animal dip compositions against the buildup of microorganisms, and in photoprocessing to prevent buildup of microorganisms, and the like.

It is known in the art that the performance of biocides may be enhanced by the combination with one or more other biocides. Thus, the compositions of this invention may be used with other biocides. Alternatively, the melting point depressants useful in this invention may also be biocides. In such a case, the compositions of the invention may contain two or more biocides.

The following specific examples are presented to illustrate the various aspects of the present invention but are not to be construed as limitations thereof. All percentages are by weight. All solvents are good commercial grade and used without further purification.

EXAMPLES

In each of the following examples, 90 g of melted 4,5-dichloro-2-octy-3-isothiazolone (which has a normal melting point of 43° C.) were mixed with 10 g of a melting point depressant. The solution was thoroughly mixed and transferred to a 100 ml glass-stoppered graduated cylinder. The cylinder was seeded with a crystal of the isothiazolone to promote crystalization, and then capped and allowed to cool to 25° C. and solidify.

The capped samples were stored at 25° C. for 16 hours and then the temperature was increased to 40° C. The resultant melts were stored at 40° C. for 8 hours. This process was repeated 4 times for a total of 5 solid/melt cycles. After the last cycle, aliquots were taken from the top and bottom of the cylinder using a Pasteur pipet, and the amount of 4,5-dichloro-2-octyl-3-isothiazolone determined.

Example 1

A sample was prepared according to the above procedure. The melting point depressant was a 1:1 mixture of methyl naphthalene and methylene chloride, specific gravity of 1.17. The amount of 4,5-dichloro-2-octyl-3-isothiazolone in both the top and bottom of the cylinder was determined and reported in Table 1.

Example 2

A sample was prepared according to the above procedure. The melting point depressant was a 34:66 mixture of methyl naphthalene and propylene carbonate, specific gravity of 1.17. The amount of 4,5-dichloro-2-octyl-3-isothiazolone in both the top and bottom of the cylinder was determined and reported in Table 1.

Example 3 (Comparative)

A sample was prepared according to the above procedure. The melting point depressant was γ-butyrolactone, specific gravity of 1.13. The amount of 4,5-dichloro-2-octyl-3-isothiazolone in both the top and bottom of the cylinder was determined and reported in Table 1.

Example 4 (Comparative)

A sample was prepared according to the above procedure. The melting point depressant was Solvesso 100 (a mixture of alkylbenzenes, with a specific gravity of 0.87). The amount of 4,5-dichloro-2-octyl-3-isothiazolone in both the top and bottom of the cylinder was determined and reported in Table 1.

TABLE 1

| | Homogeneity of Samples After 5 Solid/Melt Cycles | | |
|---|---|---|---|
| | Initial | % Isothiazolone After Solid/Melt Cycles | |
| Example | % Isothiazolone | Top | Bottom |
| 1 | 90 | 88.6 | 87.3 |
| 2 | 90 | 85.0 | 89.4 |
| 3 (comparative) | 90 | 57.5 | 85.3 |
| 4 (comparative) | 90 | 59.6 | 89.4 |

As can be seen from the above data, the compositions of the invention unexpectedly retain their homogeneity after repeated solid/melt cycles.

What is claimed is:

1. Composition useful as a highly concentrated biocide, said composition being solid at 20° C., easily meltable and solidifyable, capable of undergoing remelt and resolidification without loss of homogeneity, and comprising:

A. a first component consisting of about 99 to 50 parts of a 3-isothiazolone of the formula

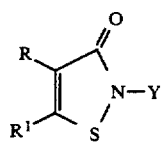

wherein R and R$^1$ are independently selected from hydrogen, halogen or R is a (C$_1$-C$_4$)alkyl group and R$^1$ is a hologen or R and R$^1$ may be joined to form an unsaturated 5- or 6-membered carbocyclic ring; Y is hydrogen, a substituted or unsubstituted (C$_1$-C$_{18}$)alkyl group, an unsubstituted or halo-substituted alkenyl or alkynyl of 2 to 8 carbon atoms, a cycloalkyl or substituted cycloalkyl of 3 to 12 carbon atoms, an aralkyl or halo-, (C$_1$-C$_4$)alkyl-, or (C$_1$-C$_4$)alkoxy-substituted aralkyl of up to 10 carbon atoms, or an aryl or halo-, (C$_1$-C$_4$)alkyl-, or (C$_1$-C$_4$)alkoxy-substituted aryl group of up to 10 carbon atoms; and B. a second component consisting of about 1 to 50 parts of a melting point depressant having a specific gravity of about 1.14 to about 1.24, or a mixture of melting point depressants having said specific gravity, said depressant or mixture being miscible in a melt of A., and being chemically compatible with A.

2. Composition according to claim 1 wherein a sufficient amount of B is added to lower the melting point of the isothiazolone by 10° C.

3. Composition according to claim 1 consisting of about 99 to 80 parts of said A.

4. Composition according to claim 1 wherein said A is 4,5-dichloro-2-octyl-3-isothiazolone or 2-octyl-3-isothiazolone.

5. Composition according to claim 1 wherein said B is a mixture of one or more hydrocarbons and one or more compounds selected from the group consisting of methylene chloride and propylene carbonate.

6. Composition according to claim 5 wherein said one or more hydrocarbons is selected from the group consisting of methyl naphthalene, phenyl xylyl ethane, bis(methylethyl)-1,1-biphenyl, and mixtures of mono-, di-, and tri-isopropylbiphenyl.

7. Composition according to claim 1 consisting essentially of A and B.

8. Composition according to claim 1 wherein said A is selected from the group consisting of 4,5-dichloro-2-octyl-3-isothiazolone, 2-octyl-3-isothiazolone, 5-chloro-2-methyl-3-isothiazolone, and 2-methyl-3-isothiazolone.

9. Composition according to claim 1 wherein a sufficient amount of said B is added to lower the melting point of the isothiazolone by 5° C.

10. Method of incorporating a 3-isothiazolone biocide which is normally solid at 20° C. in, on, or at a locus to be protected by said biocide comprising providing a composition according to claim 1, melting said composition to form a melt, using part of said melt either (a) in a solution for delivery to a locus, or (b) directly in, on, or at a locus, and allowing the remaining part of said melt to cool and resolidify.

* * * * *